United States Patent [19]

Light et al.

[11] 4,076,854
[45] Feb. 28, 1978

[54] FLAVORING WITH A CYCLOHEXADIENE DERIVATIVE

[75] Inventors: Kenneth K. Light, Long Branch; Bette M. Spencer, Ocean Grove; Joaquin F. Vinals, Red Bank, all of N.J.; Jacob Kiwala, Brooklyn, N.Y.; Manfred Hugo Vock, Locust, N.J.; Edward J. Shuster, Brooklyn, N.Y.

[73] Assignee: International Flavors & Fragrances Inc., New York, N.Y.

[21] Appl. No.: 774,058

[22] Filed: Mar. 3, 1977

[51] Int. Cl.² ............................................. A23L 1/226
[52] U.S. Cl. .................................... 426/538; 252/522; 260/586 R; 131/17 R
[58] Field of Search ...................... 260/586 R; 426/538

[56] References Cited

U.S. PATENT DOCUMENTS

| | | | |
|---|---|---|---|
| 3,923,898 | 12/1975 | Schulte-Elte | 426/538 X |
| 3,927,107 | 12/1975 | Schulte-Elte | 426/538 X |
| 3,957,877 | 5/1976 | Schulte-Elte | 260/586 R |
| 3,962,148 | 6/1976 | Hochstetler | 260/586 R X |
| 3,989,857 | 11/1976 | Demole | 426/538 X |
| 4,029,106 | 6/1977 | Demole | 426/538 X |

Primary Examiner—Joseph M. Golian
Attorney, Agent, or Firm—Arthur L. Liberman; Franklin D. Wolffe

[57] ABSTRACT

Processes and compositions are described for use in foodstuff, chewing gum, toothpaste and medicinal product flavor and aroma; tobacco flavor and aroma; perfume and perfumed article aroma augmenting, enhancing and imparting compositions; and as foodstuff, chewing gum, toothpaste, medicinal product, tobacco, perfume and perfumed article aroma imparting materials of one or more cyclohexadiene derivatives having the generic formula:

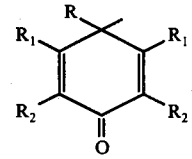

wherein R is one of $C_1$–$C_5$ alkyl, $R_1$ is methyl when $R_2$ is hydrogen, and $R_1$ is hydrogen when $R_2$ is methyl.

2 Claims, 7 Drawing Figures

IR SPECTRUM ACCORDING TO EXAMPLE II

FIG. 5 NMR SPECTRUM ACCORDING TO EXAMPLE IV
SOLVENT: CDCl₃
SWEEP WIDTH: 1000 Hz.

NMR SPECTRUM ACCORDING TO EXAMPLE V

SOLVENT: CDCl$_3$
SWEEP WIDTH: 2000 Hz.

FLAVORING WITH A CYCLOHEXADIENE DERIVATIVE

BACKGROUND OF THE INVENTION

The present invention relates to cyclohexadiene derivatives having the formula:

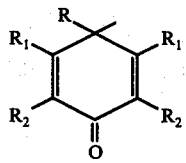

wherein R is one of $C_1$–$C_5$ alkyl, $R_1$ is methyl when $R_2$ is hydrogen, and $R_1$ is hydrogen when $R_2$ is methyl, produced by the processes of our invention and novel compositions using one or more of such cyclohexadiene derivatives to augment or enhance the flavor and/or aroma of consumable materials or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product.

Sweet, hay-like, heliotropine-like, black pepper-like, woody, tobacco-like and "Oriental" aroma characteristics with sweet, hay-like, heliotropine-like, black pepper-like, woody, tobacco, "Oriental" flavor characteristics are particularly desirable for many uses in foodstuff flavorings, chewing gum flavors, toothpaste flavors, and medicinal product flavors.

Warm, sweet, slightly minty, woody, natural green, herbaceous, Jasmine-like, fruity aromas are desirable in several types of perfume compositions, perfumed articles, and colognes.

"Dry black tobacco-like" notes, spicy notes, celery-like notes, black pepper-like notes, sweet notes and Virginia tobacco-like notes prior to and on smoking in both the main stream and side stream, are desirable in tobaccos and tobacco flavors.

In the paper by Demole and Enggist, *Helv. Chim. Acta.* 57(Fasc. 7):2087–2091 (1974), compounds having the following structures have been found to be present in Burley tobacco flavor:

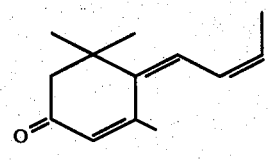

4a  4b

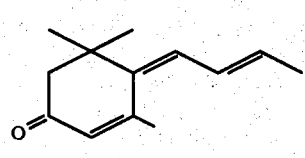

4c  4d

None of the compounds of Demole and Enggist have properties bearing any relationship to the properties of the cyclohexadiene derivatives of the instant application.

THE INVENTION

Figure 1:
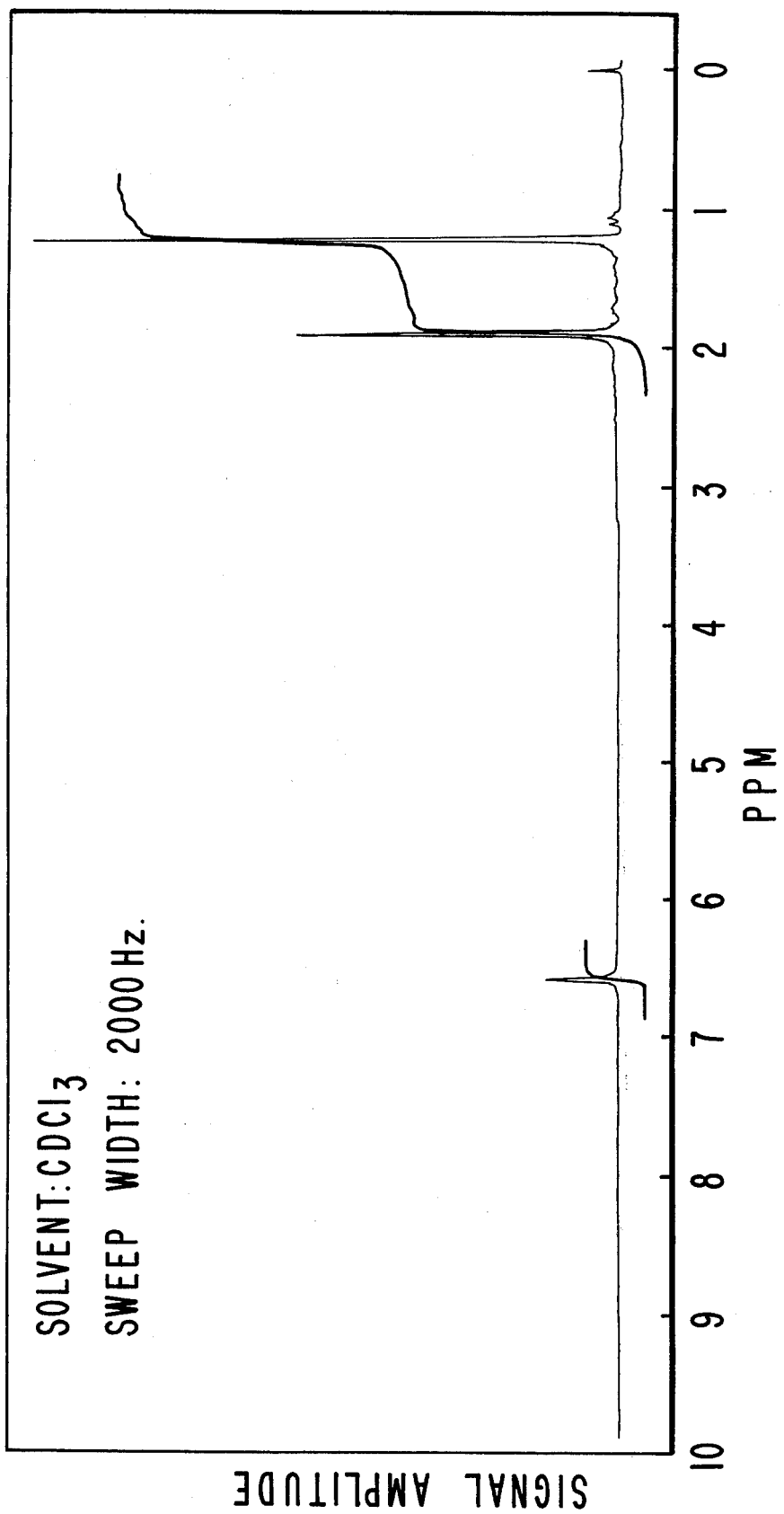
FIG. 1 represents the NMR spectrum for the compound 2,4,4,6-tetramethylcyclohexa-2,5-diene-1-one, produced according to Example II.

It has now been discovered that novel solid and liquid foodstuff, chewing gum, medicinal product and toothpaste compositions and flavoring compositions therefor having sweet, hay-like, heliotropine-like, black pepper-like, woody, tobacco-like and "Oriental" aroma characteristics with sweet, hay-like, heliotropine-like, black pepper-like, woody, tobacco, "Oriental" flavor characteristics; novel perfume compositions, colognes and perfumed articles having warm, sweet, slightly minty, woody, natural green, herbaceous, Jasmine-like, fruity aromas; and novel tobacco and tobacco flavor compositions having "dry black tobacco-like" notes, spicey notes, celery-like notes, black pepper-like notes, sweet notes and Virginia tobacco-like notes prior to and on smoking in both the main stream and side stream, may be provided by the utilization of cyclohexadiene derivatives having the formula:

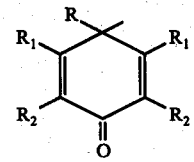

wherein R is one of $C_1$–$C_5$ alkyl, $R_1$ is methyl when $R_2$ is hydrogen, and $R_1$ is hydrogen when $R_2$ is methyl, in foodstuffs, chewing gums, toothpastes, medicinal product flavors, perfumes, colognes, perfumed articles, tobaccos and tobacco flavors.

The cyclohexadiene derivatives useful as indicated herein may be produced according to one of the following processes:

(1) Reacting an alkyl-trimethylcyclohexa-1,3-diene with oxygen in the presence of light, an ultraviolet sensitizer and a basic catalyst and fractionally distilling the resulting product. This process is illustrated by the following reaction:

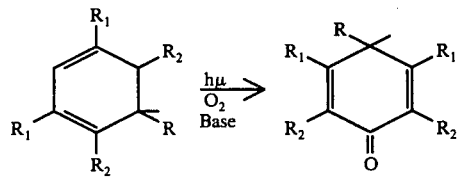

(2) Reacting a 4-alkyl-4-hydroxy-3,5,5-trimethyl-2-cyclohexen-1-one with dilute aqueous mineral acid and distilling the resulting reaction product. This process can be illustrated by the following reaction:

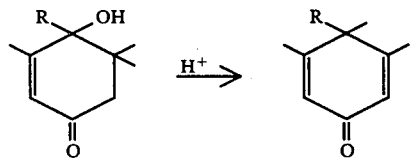

The photo-oxidation reaction is preferably carried out in an inert solvent such as methanol or a methanol-benzene mixture in the presence of a reaction sensitizer such as rose bengal and a base such as sodium hydroxide and potassium hydroxide. The photo-oxidation is carried out by bubbling oxygen through the reaction mass. The time of reaction as well as the rate of reaction is a function of the following variables:

1. Bubble size of oxygen;
2. Throughput of oxygen per unit of time;
3. Pressure;
4. Concentration of base in reaction mass; and
5. Concentration of UV sensitizer in reaction mass.

Higher pressure give rise to longer oxygen residence time thereby permitting shorter times of reaction and greater yields per unit time. Higher concentrations of reaction sensitizer give rise to faster reaction rates; up to sensitizer concentrations of 0.5 gm per liter and sensitizer:diene reactant weight ratios of 0.5:4, whereas any further increase in sensitizer concentrations does not give rise to any material increase in reaction rate. It is preferable to carry out the photo-oxidation reaction at a temperature of between 15° C and 70° C with room temperature being most convenient.

The second of the above reaction sequences may be carried out using a mineral acid, for example dilute aqueous hydrochloric acid, sulfuric acid or phosphoric acid. Preferably the reaction is carried out in the presence of an inert solvent such as hexane or cyclohexane, at a temperature in the range of from 15° C up to 70° C, most conveniently at room temperature.

At the end of each of the foregoing reactions, the reaction mass is distilled in fractional distillation apparatus yielding the desired product.

Organoleptic properties of materials produced according to the above-mentioned processes are as follows:

TABLE I

| Compound | Structure | Organoleptic Properties |
|---|---|---|
| 2,4,4,6-tetra-methylcyclohexa-2,5-diene-1-one | | Flavor: medicinal |
| | | Fragrance: warm, sweet, slightly minty, woody aroma with natural green and hay-like nuances |
| | | Tobacco: Virginia tobacco-like |
| 4-butyl-3,4,5-trimethyl-2,5-cyclohexa-diene-1-one | | Flavor: sweet, hay-like, heliotropine-like, black pepper-like, woody, tobacco-like and "Oriental" aroma characteristics with sweet, hay-like, heliotropine-like, black pepper-like, woody, tobacco, "Oriental" flavor characteristics |
| | | Fragrance: sweet, honey-like celery note with tobacco and floral nuances and a distinct Jasmine undertone |
| | | Tobacco: dry black tobacco notes as well as pungent, spicey, celery, black pepper-like and sweet notes, both prior to and on smoking, in the main stream as well as the side stream |

When the cyclohexadiene derivatives of our invention are used as food flavor adjuvants, the nature of the co-ingredients included with each of the said cyclohexadiene derivatives in formulating the product composition will also serve to alter, modify, augment or enhance the organoleptic characteristics of the ultimate foodstuff treated therewith.

As used herein in regard to flavors, the terms "alter," "modify," and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character, or taste."

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber, or certain comestible natural or synthetic resins or waxes. Incorporated with the gum base in admixture therewith may be plasticizers or softening agents, e.g., glycerine; and a flavoring composition which incorporates the cyclohexadiene derivative(s) of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise nondeleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxytoluene (2,6-tertiary-butyl-4-methylphenol), propyl gallate and the like; and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin; proteinaceous materials lipids; carbohydrates; starches; pectins; and emulsifiers, e.g., mono- and diglycerides of fatty acids, skim milk powder, hexoses, pentoses; disaccharides,, e.g., sucrose corn syrup and the like.

Surface active agents include emulsifying agents, e.g., fatty acids such as capric acid, caprylic acid, palmitic acid, myrisitic acid and the like; mono- and diglycerides of fatty acids; lecithin; deforming and flavor-dispersing agents such as sorbitan monostearate, potassium stearate, hydrogenated tallow alcohol and the like.

Conditions include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lacetate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta, beta-dimethyl-acrolein, methyl-n-amyl ketone, 2-hexenal, isopentanal, hydrocinnamic aldehyde, cis-3-hexenal, 2-heptenal, nonyl aldehyde, 4(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanol; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2- hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethylnaphthalene, dodecane, methyldiphenyl, methyl-naphthalene, myrcene, naphthalene, octadecane, tetradecane, tetramethylnephthalene, tridecane, trimethylnaphthalene, undecane, caryophyllene, 1-phellandrene, p-cymene, 1-alpha-pinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, rose absolute, orris absolute, lemon essential oil, Bulgarian rose, yara yara and vanilla, lactones such as δ-nonalactone; sulfides, e.g., methyl sulfide and other materials such as maltol, and acetals (e.g., 1,1-diethoxy-ethane, 1,1-dimethoxy-ethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the cyclohexadiene derivative(s) of our invention by not covering or spoiling the organoleptic properties (aroma and/or taste) thereof; (ii) be non-reactive with the cyclohexadiene derivative(s) of our invention, and (iii) be capable of providing an environment in which the cyclohexadiene derivative(s) can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered, or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the cyclohexadiene derivative(s) employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of the cyclohexadiene derivative(s) will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of the cyclohexadiene derivative(s) ranging from a small but effective amount, e.g., 0.5 parts per million up to about 100 parts per million based on total composition, are suitable. Concentrations in excess of the maximum quantity stated are not normally recommended since they fail to prove commensurate enhancement of organoleptic properties. In those instances wherein a cyclohexadiene derivative is added to the foodstuff as an integral component of a flavoring composition, it is, of course, essential that the total quantity of flavoring composition employed be sufficient to yield an effective concentration in the foodstuff product.

Food flavoring compositions prepared in accordance with the present invention preferably contain the cyclohexadiene derivative(s) in concentrations from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the cyclohexadiene derivative(s) with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix, are obtained by mixing the dried components, e.g., starch, sugar and the like and the cyclohexadiene derivative(s) in a dry blender until the requisite degree of uniformity is achieved.

It is presently preferred to combine with the cyclohexadiene derivative(s) of our invention the following adjuvants:

p-Hydroxybenzyl acetone;
Geraniol;
Cassia oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl anthranilate;
5-Methylfurfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
Damascone (1-crotonyl-2,2,6-trimethylcyclohexen-1-one);
Damascenone (1-crotonyl-2,2,6-trimethylcyclohexa-1,5-diene);
Beta-cyclohomocitral (2,2,6-trimethylcyclohex-1-ene carboxaldehyde);
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxybenzene);
2-(4-Hydroxy-4-methylpentyl)-norbornadiene prepared according to Example II of U.S. Pat. No. 3,911,028 issued on Oct. 7, 1975;
Reaction product of L-proline and 4-hydroxy-2,5-dimethyl-2(H)-furan-3-one (as produced according to Example I of U.S. Pat. No. 3,782,973 issued on Jan. 1, 1974);
Reaction product of L-proline with 4-hydroxy-2,5-dimethyl-2(H)-furan-3-one (produced according to Example II of U.S. Pat. No. 3,782,973 issued on Jan. 1, 1974);
Reaction product of L-proline with 4-hydroxy-2,5-dimethyl-2(H)-furan-3-one (produced according to Example III of U.S. Pat. No. 3,782,973 issued on Jan. 1, 1974);

Reaction product of L-proline with 4-hydroxy-2,5-dimethyl-2(H)-furan-3-one (produced according to Example IV of U.S. Pat. No. 3,782,973 issued on Jan. 1, 1974);

Reaction product of ethyl maltol with L-proline (produced according to Example VI of U.S. Pat. No. 3,782,973 issued on Jan. 1, 1974);

Reaction product of cyclotene with L-proline (produced according to Example VIII of U.S. Pat. No. 3,782,973 issued on Jan. 1, 1974); and Reaction product of ethyl cyclotene with L-proline (produced according to Example IX of U.S. Pat. No. 3,782,973 issued on Jan. 1, 1974).

the cyclohexadiene derivative(s) of our invention and one or more auxiliary perfume ingredients, including, for example, alcohols, aldehydes, nitriles, esters, cyclic esters and natural essential oils, may be admixed so that the combined odors of the individual components produce a pleasant and desired fragrance, particularly and preferably honey and Jasmine fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually-low boiling, fresh-smelling materials.

In perfume compositions, it is the individual components which contribute to their particular olfactory characteristics, however the overall sensory effect of the perfume composition will be at least the sum total of the effects of each of the ingredients. Thus, one or more of the cyclohexadiene derivative(s) can be used to alter, modify or enhance the aroma characteristics of a perfume composition, for example, by utilizing or moderating the olfactory reaction contributed by another ingredient in the composition.

The amount of cyclohexadiene derivative(s) of our invention which will be effective in perfume compositions as well as in perfumed articles and colognes depends on many factors, including the other ingredients, their amounts and the effects which are desired. It has been found that perfume compositions containing as little as 0.01% of a cyclohexadiene derivative(s) or even less (e.g., 0.005%) can be used to impart warm, sweet, slightly minty, woody, natural green, herbaceous, Jasmine-like, fruity aromas to soaps, cosmetics or other products. The amount employed can range up to 70% of the fragrance components and will depend on considerations of cost, nature of the end product, the effect desired on the finished product and the particular fragrance sought.

The cyclohexadiene derivative(s) of our invention is (are) useful as an olfactory component(s) in detergents and soaps, space odorants and deodorants, perfumes, colognes, toilet water, bath preparations such as lacquers, brilliantines, pomades and shampoos, cosmetic preparations such as creams, deodorants, hand lotions and sun screens; powders such as talcs, dusting powders, face powders and the like. When used as an olfactory component(s), as little as 1% of cyclohexadiene derivative(s) will suffice to impart an intense floral note to honey or Jasmine formulations. Generally no more than 3% of cyclohexadiene derivative based on the ultimate end product is required in the perfume composition.

In addition, the perfume composition or fragrance composition of our invention can contain a vehicle or carrier for the cyclohexadiene derivative(s). The vehicle can be a liquid such as a non-toxic alcohol, a non-toxic glycol, or the like. The carrier can also be an absorbent solid, such as a gum (e.g., gum arabic) or components for encapsulating the composition (such as gelatin).

An additional aspect of our invention provides an organoleptically improved smoking tobacco product and additives therefor including methods of making the same which overcome problems heretofore encountered in the creation or enhancement of specific desired "dry black tobacco-like" notes, spicey notes, celery-like notes, black pepper-like notes, sweet notes and Virginia tobacco-like notes. These notes, both prior to and on smoking, in both the main stream and the side stream, may now be readily controlled and maintained at the desired uniform level regardless of variations in the tobacco components of the blend; or the nature of the filter used in conjunction with the smoking tobacco article.

This invention further provides improved tobacco additives and additives for materials used in the fabrication of tobacco articles (particularly smoking tobacco articles) and methods whereby desirable "dry black tobacco-like" notes, spicey notes, celery-like notes, black pepper-like notes, sweet notes and Virginia tobacco-like notes prior to and on smoking, in both the main stream and the side stream, may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient, one or more of the cyclohexadiene derivatives of our invention.

In addition to the cyclohexadiene derivatives of our invention, other flavoring and aroma additives may be added to the smoking tobacco material or substitute therefor either separately or in mixture with one or more of the cyclohexadiene derivatives:

I. Synthetic materials
 Beta-methylcinnamaldehyde;
 Eugenol;
 Dipentene;
 Damascenone;
 Maltol;
 Ethyl maltol;
 Delta-undecalactone;
 Delta-decalactone;
 Benzaldehyde;
 Amyl acetate;
 Ethyl butyrate;
 Ethyl valerate;
 Ethyl acetate
 2-Hexen-1-ol;
 2-Methyl-5-isopropyl-1,3-nonadiene-8-one;
 2-Methyl-5-isopropylacetophenone;
 2-Hydroxy-2,5,5,8a-tetramethyl-1-(2-hydroxyethyl)-decahydronaphthalene;
 Dodecahydro-3a,6,6,9a-tetramethylnaphtho(2,1-b)-furan;
 4-Hydroxyhexanoic acid, gamma-lactone;

Polyisoprenoid hydrocarbons defined in Example V of U.S. Pat. No. 3,589,372 issued on June 29, 1971.

II. Natural Oils

Celery seed oil;
Coffee extract;
Bergamot oil;
Cocoa extract;
Nutmeg oil;
Origanum oil.

An aroma of flavoring concentrate containing one or more of the cyclohexadiene derivatives of our invention and, if desired, one or more of the above-indicated additional flavoring additives may be added to the smoking tobacco material, to the filter or to the leaf or paper wrapper or to a filter which is part of the smoking article. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste, but insofar as enhancement or the imparting of "dry black tobacco-like" notes, spicey notes, celery-like notes, black pepper-like notes, sweet notes and Virginia tobacco-like notes prior to and on smoking, in both the main stream and the side stream, we have found that satisfactory results are obtained if the proportion by weight of the sum total of cyclohexadiene derivative to smoking tobacco material is between 50 ppm and 1500 ppm (0.005% – 0.15%) of the active ingredients to the smoking tobacco material. We have further found that satisfactory results are obtained if the proportions by weight of the sum total of cyclohexadiene derivative used to flavoring material is between 0.05:1 and 0.50:1.

Any convenient method for incorporating the cyclohexadiene derivative(s) in the tobacco product may be employed. Thus the cyclohexadiene derivative(s) taken alone or along with other flavoring additives may be dissolved in a suitable solvent such as ethanol, pentane, diethyl ether and/or other volatile organic solvents, and the resulting solution may either be sprayed on the cured, cased and blended tobacco material; or the tobacco material or filter may be dipped into such solution. Under certain circumstances a solution of cyclohexadiene derivative(s) taken alone or taken further together with other flavoring additives as set forth above, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated, and the thus-treated tobacco may be blended with other tobaccos before the ultimate tobacco product is formed. In such cases the tobacco treated may have one or more cyclohexadiene derivative(s) of our invention in excess of the amounts or concentrations above indicated so that when blended with other tobaccos, the final product will have the percentage within the indicated range.

In accordance with one specific example of our invention an aged, cured and shredded domestic burley tobacco is sprayed with a 20% ethyl alcohol solution of a 50:50 mixture of 2,4,4,6-tetramethylcyclohexa-2,5-diene-1-one and 4-butyl-3,4,5-trimethyl-2,5-cyclohexadiene-1-one in an amount to provide a tobacco composition containing 600 ppm by weight of 2,4,4,6-tetramethylcyclohexa-2,5-diene-1-one and 600 ppm of 4-butyl-3,4,5-trimethyl-2,5-cyclohexadien-1-one on a dry basis. Thereafter the alcohol is removed by evaporation, and the tobacco is manufactured into cigarettes by the usual techniques. The cigarette when treated as indicated has desired and pleasing "dry black tobacco-like," spicey, celery-like, black pepper-like, sweet and Virginia tobacco-like notes which are detectable in the main stream and side streams when the cigarette is smoked.

While our invention is particularly useful in the manufacture of smoking tobacco such as cigarette tobacco, cigar tobacco and pipe tobacco, other tobacco products formed from sheeted tobacco dust or fines may also be used. As stated supra, the cyclohexadiene derivative(s) of our invention can be incorporated with materials such as filter tip materials, seam paste, packaging materials and the like which are used along with the tobacco to form a product adapted for smoking. Furthermore the cyclohexadiene derivative(s) of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

It will thus be apparent that the cyclohexadiene derivative(s) of our invention can be utilized to alter, modify or enhance sensory properties, particularly organoleptic properties, such as flavor(s) and/or fragrance(s) of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

PREPARATION OF 1,3,5,5-TETRAMETHYLCYCLOHEXA-1,3-DIENE

Reaction:

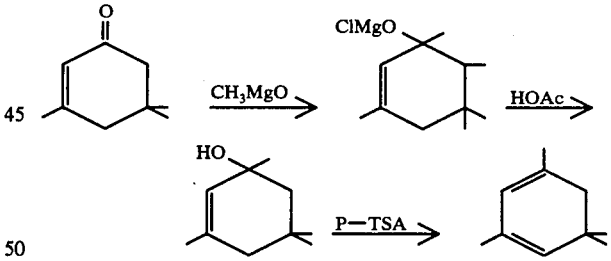

To a 5-liter flask fitted with stirrer, thermometer, dropping funnel, reflux condenser, drying tube and nitrogen purge is charged 2100 ml(6.3 moles) of a 3 m solution of methyl magnesium chloride in tetrahydrofuran. The flask and contents are cooled to 0° C, and 730 g (5.3 moles) of isophorone is added at 0°–5° C over a two-hour period. The mixture is allowed to warm to room temperature and to stand overnight. The reaction mixture is poured over a mixture of 2800 g of ice and 370 g of glacial acetic acid. When all the ice has melted, the layers are separated and the organics are washed twice with 500 ml of water. The solvent is removed on a rotary evaporator, and the product is transferred to a 2-liter flask fitted with a condenser and a water separator. Benzene (300 ml) and p-toluenesulfonic acid (0.5 g) are added, and the mixture is refluxed until no additional water is separated. The product is distilled on a 12 inches Goodloe column using a reflux ratio of 9:1. A total of 494 g of product is obtained (boiling point 66°–67° C at 42 mm Hg) which is predominantly 1,3,5,5-tetramethylcyclohexa-1,3-diene.

EXAMPLE II

PREPARATION OF 4-HYDROXY-2,4,6,6-TETRAMETHYLCYCLOHEX-2-EN-1-ONE AND 2,4,4,6-TETRAMETHYLCYCLOHEXA-2,5-DIENE-1-ONE

Reaction

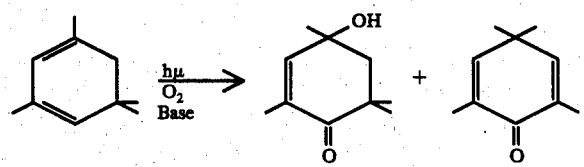

A solution of 40 g (0.3 moles) of 1,3,5,5-tetramethylcyclohexa-1,3-diene (prepared as in Example I), 13 g (0.23 moles) of potassium hydroxide, and 0.3 g of Rose Bengal in 600 ml of methanol is placed in a flask and irradiated at a temperature of 25°–28° C with a 450 watt tungsten photo lamp over a period of two hours. A steady stream of oxygen is bubbled through the solution during irradiation. At the end of the two-hour irradiation period, analysis of a sample of the reaction mixture by GLC (10 feet × ⅛ inches 10% Carbowax 20M on Chromasorb W, programmed from 80°–220° C at 8°/min.) shows that the starting material is completely consumed and two products have formed. Both products are trapped from the GLC column and analyzed. The first (about 20% of the reaction product) is found to be 2,4,4,6-tetramethylcyclohexa-2,5-diene-1-one (Compound A) and exhibits the following spectral properties:

| NMR (δ) ppm | Interpretation |
|---|---|
| 1.2 | (s, 6H) |
| 1.9 | (s, 6H) |
| 6.58 | (2, 2H) |

Infrared spectrum: 1630 cm$^{-1}$ (C{O)
Mass Spectral Analysis (m/e): 107, 150 (m), 135, 39, 41, 91.

Figure 2:
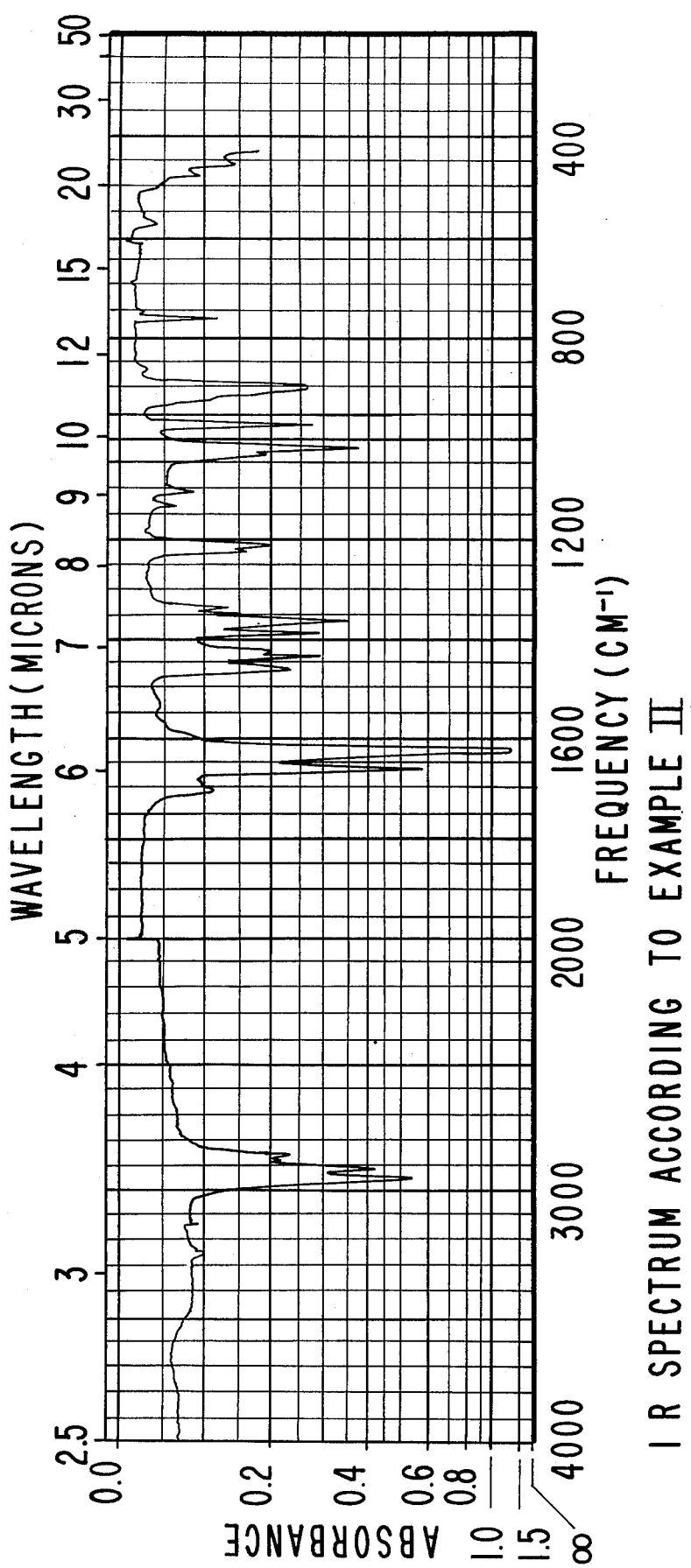
FIG. 2 represents the IR spectrum for the compound 2,4,4,6-tetramethylcyclohexa-2,5-diene-1-one, produced according to Example II.

FIG. 1 is the NMR spectrum for Compound A. FIG. 2 is the IR spectrum for compound A.

The second (about 80% of the product mixture) is found to be 4-hydroxy-2,4,6,6-tetramethylcyclohex-2-en-1-one (Compound B) and exhibits the following spectral properties:

| NMR (δ) ppm | Interpretation |
|---|---|
| 1.16 | (s, 3H) |
| 1.28 | (s, 3H) |
| 1.44 | (s, 3H) |
| 1.81 | (d, 3H) |
| 2.02 | (s, 2H) |
| 6.41 | (d, 1H) |

Infrared spectrum: 1630 cm$^{-1}$ (C{O)
Mass Spectral Analysis (m/e): 112, 69, 43, 39, 41, 84

Figure 3:
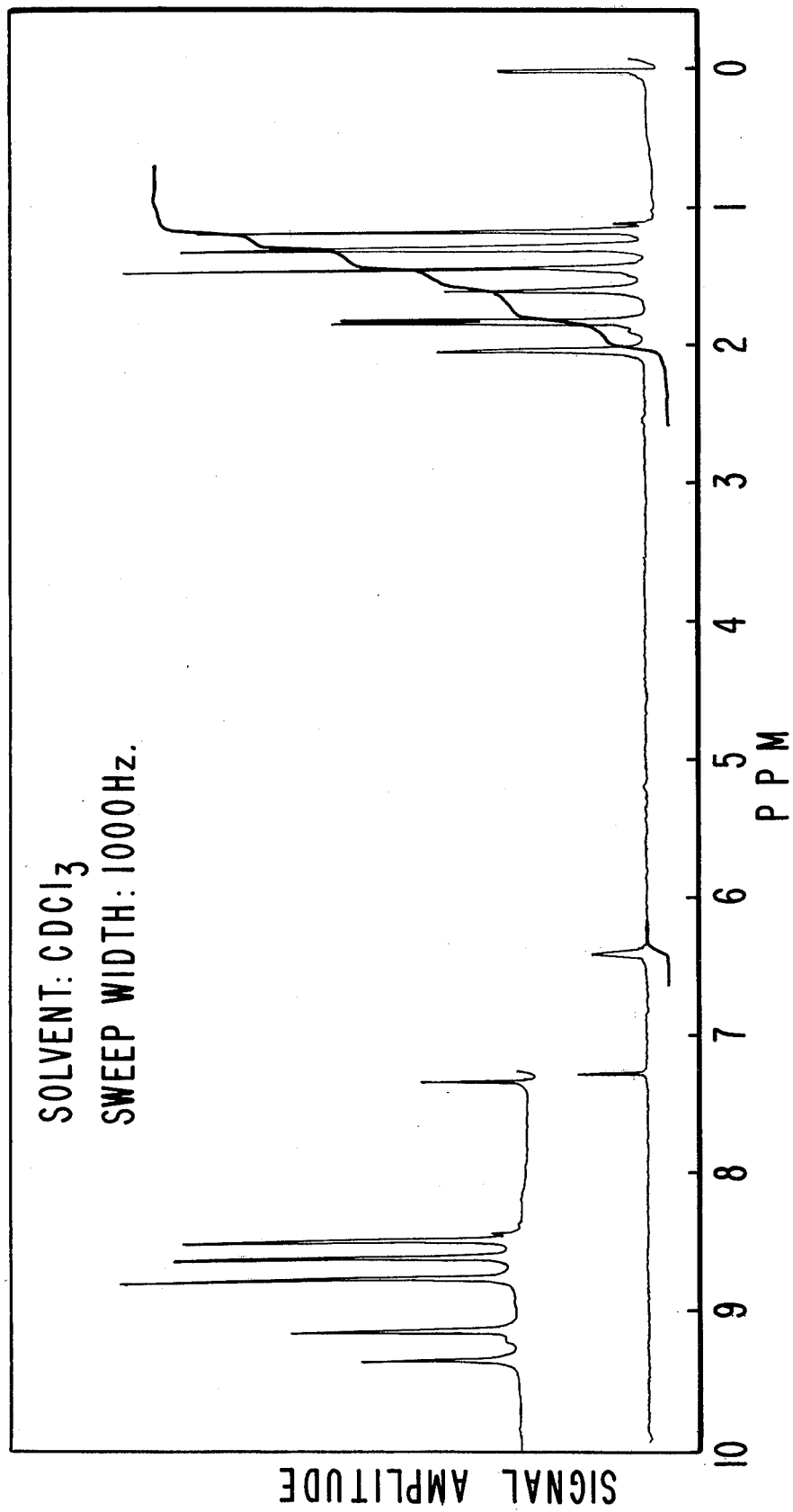
FIG. 3 represents the NMR spectrum for the compound 4-hydroxy-2,4,6,6-tetramethylcyclohex-2-en-1-one, produced according to Example II.
Figure 4:
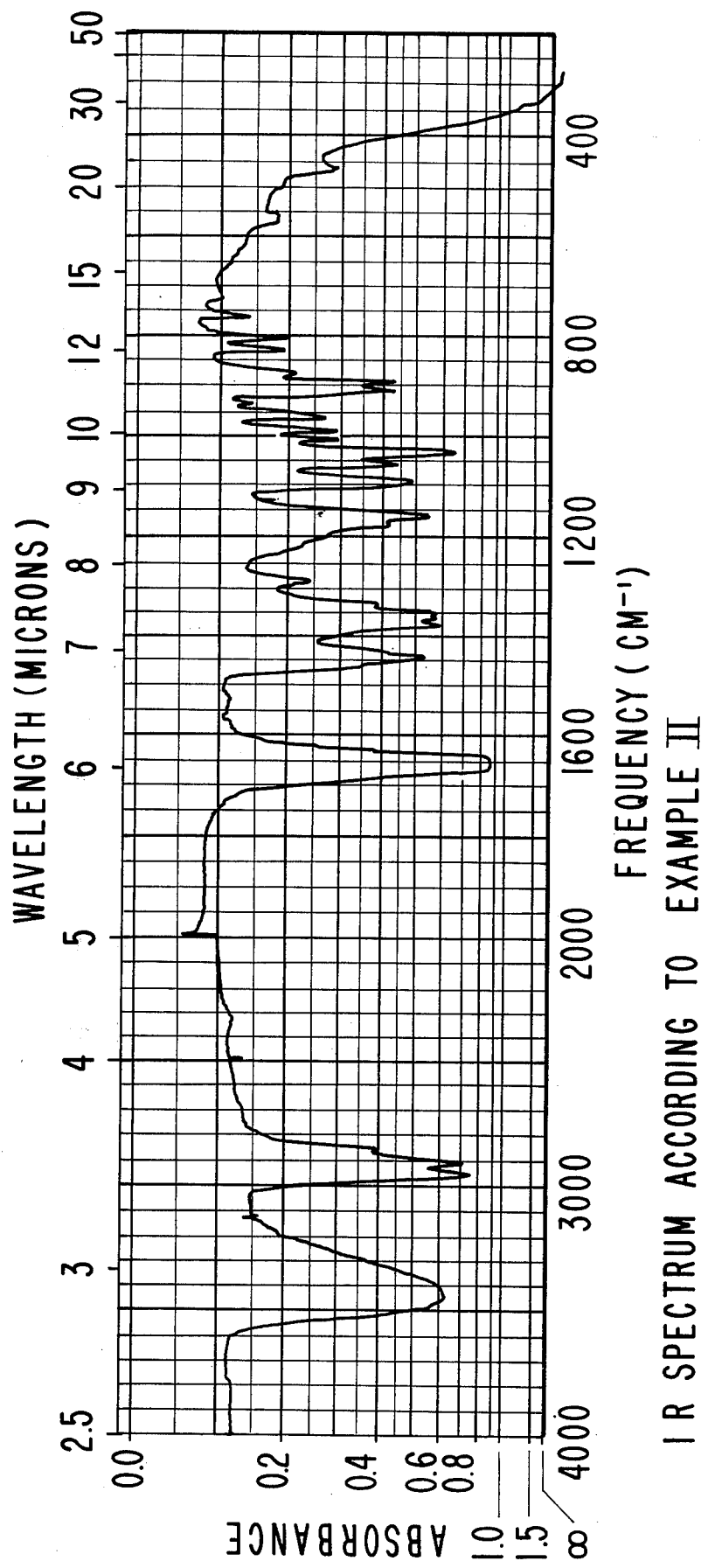
FIG. 4 represents the IR spectrum for the compound 4-hydroxy-2,4,6,6-tetramethylcyclohex-2-en-1-one, produced according to Example II.

FIG. 3 is the NMR spectrum for Compound B. FIG. 4 is the IR spectrum for Compound B.

The reaction mixture is poured into 500 ml of water, and the organics are extracted with four 100 ml portions of ether. The ether is removed by means of a rotary evaporator, and the two products are separated by means of a careful distillation. Compound A is obtained first and has a boiling point of 60° C at 1.5 mm Hg. Compound B distills second with a boiling point of 100° C at 1.5 mm Hg.

EXAMPLE III

PREPARATION OF 2,7,9,9-TETRAMETHYL-1,4-DIOXASPIRO-[4,5]DEC-6-EN-8-ONE

Reaction:

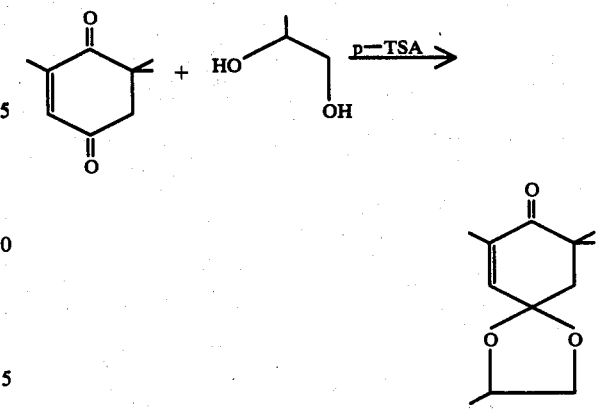

To a 2-liter flask fitted with a reflux condenser, a water separator and a stirrer is charged 265 g of 2,6,6-trimethylcyclohex-2-en-1,4-dione (prepared by the method described in Helv. Chim. Acta, 39:2041 [1956]), 266 g of propylene glycol, 500 ml of benzene and 1 g of p-toluenesulfonic acid. The reactants are stirred and refluxed until no additional water is collected in the water separator. The product is washed with water to a pH of 6, and the solvent is stripped off. The residue is vacuum distilled through a 9 inches Goodloe column to yield 257 g of product, boiling point 92° C at 1 mm Hg (80% yield).

EXAMPLE IV

PREPARATION OF 4-BUTYL-4-HYDROXY-3,5,5-TRIMETHYL-2-CYCLOHEXEN-1-ONE

Reaction:

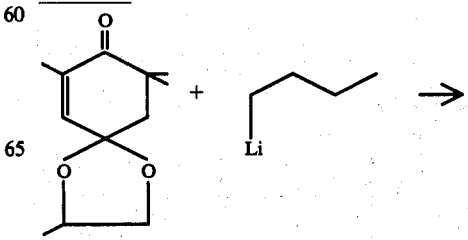

-continued

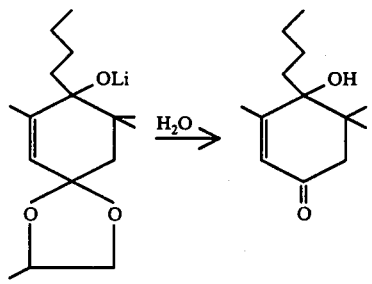

A solution of 20 g of 2,7,9,9-tetramethyl-1,4-dioxaspiro[4,5]dec-6-en-8-one (prepared by the method of Example III) in hexane is stirred while a solution of n-butyl lithium in hexane is added dropwise. When no additional exotherm occurs, the addition is stopped and the mixture is stirred for about 15 minutes. Water is added with stirring to hydrolyze the lithium salt. The organic layer is separated, and the hexane is allowed to evaporate leaving oily crystals which are recrystallized from cyclohexane yielding 10 g of 4-butyl-4-hydroxy-3,5,5-trimethyl-2-cyclohexyl-1-one, melting point 90°–93° C. The compound exhibits the following spectral characteristics:

| NMR (δ) ppm | Interpretation |
|---|---|
| 0.87 | (t, 3H) |
| 1.02 | (s, 3H) |
| 1.05 | (s, 3H) |
| 1.05–2.1 | (complex signals, 4H) |
| 1.98 | (s, 3H) |
| 2.35 | (q, 4H) |

Infrared analysis: 1640 cm$^{-1}$ (C=O)

Mass Spectral Analysis (m/e): 43, 41, 29, 39, 27, 28, 11, 154, 210 (m).

Figure 5:
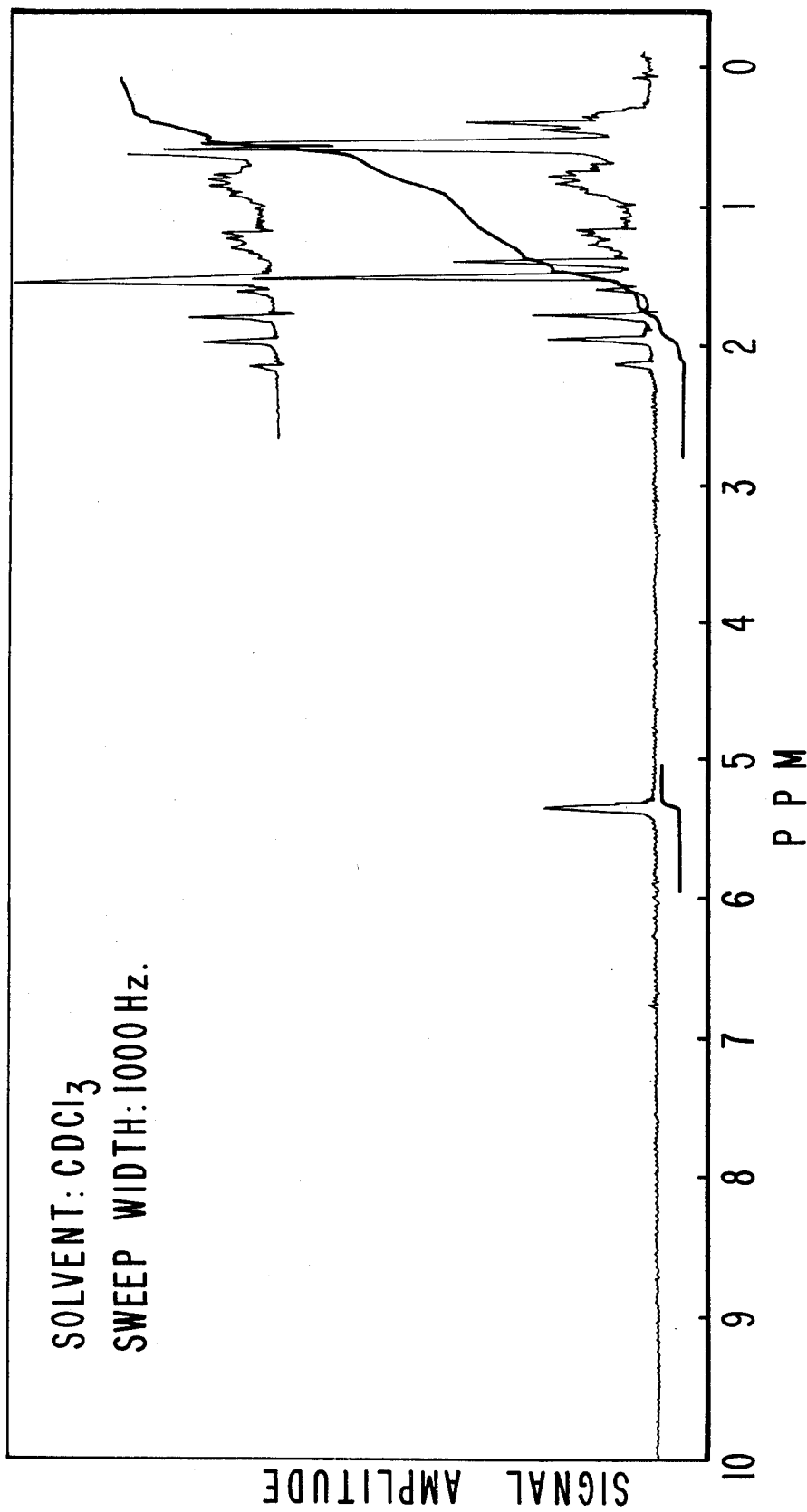
FIG. 5 represents the NMR spectrum for the compound 4-butyl-4-hydroxy-3,5,5-trimethyl-2-cyclohexen-1one, produced according to Example IV.
Figure 6:
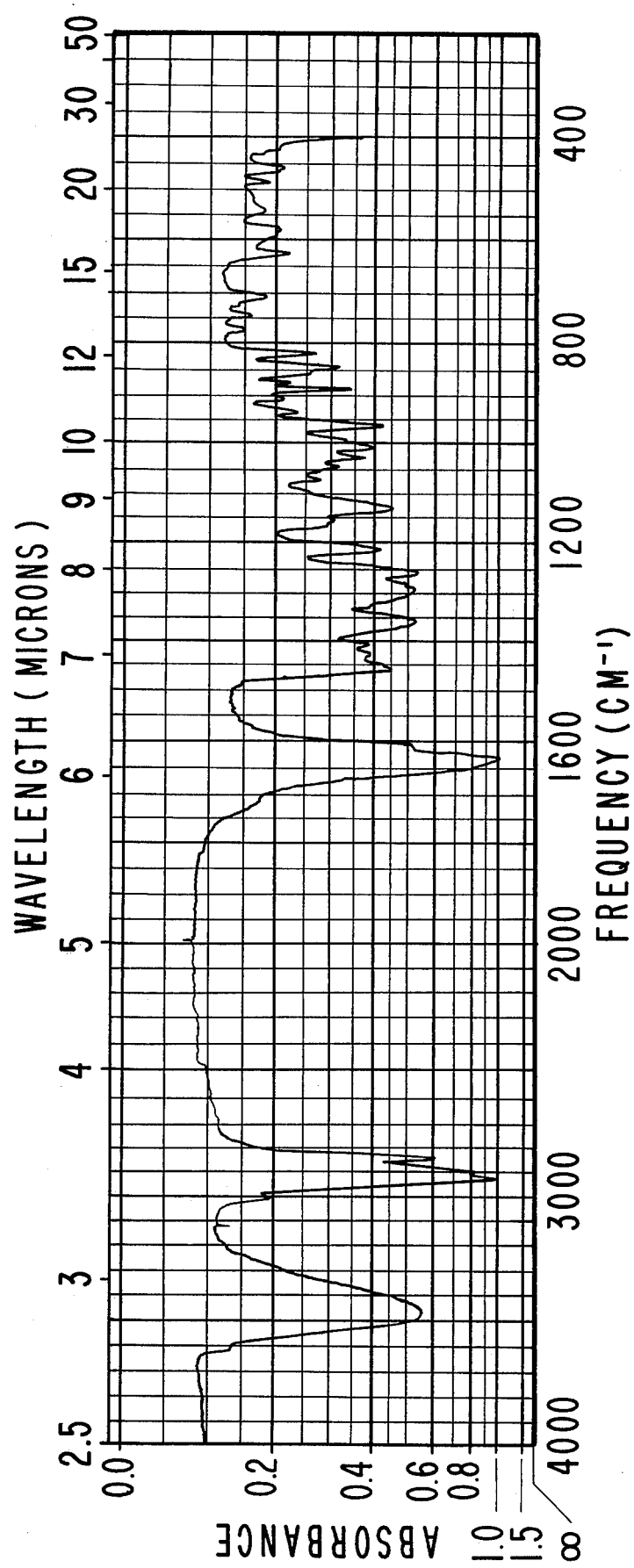
FIG. 6 represents the IR spectrum for the compound 4-butyl-4-hydroxy-3,5,5-trimethyl-2-cyclohexen-1-one, produced according to Example IV.

FIG. 5 is the NMR spectrum. FIG. 6 is the IR spectrum.

EXAMPLE V

PREPARATION OF 4-BUTYL-3,4,5-TRIMETHYL-2,5-CYCLOHEXADIEN-1-ONE

Reaction:

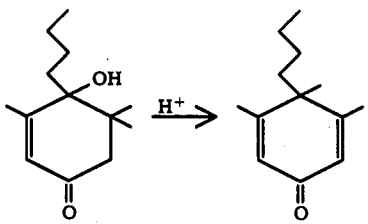

A solution of 7 g of 4-butyl-4-hydroxy-3,5,5-trimethyl-2-cyclohexen-1-one (prepared by the procedure of Example IV) in hexane is stirred overnight with 10 ml of a 5% solution of HCl. The hexane is separated and evaporated, and the residue is distilled through a micro column using triethanolamine as a still base. The product obtained is 4-butyl-3,4,5-trimethyl-2,5-cyclohexadien-1-one, boiling point 112°–119° C at 0.1 mm Hg. The compound exhibits the following spectral characteristics:

| NMR (δ) ppm (CdCl$_3$) | Interpretation |
|---|---|
| 0.85 | (t, 3H) |
| 1.26 | (s, 3H) |
| 1.0–2.0 | (complex signals, 4H) |
| 2.00 | (s, 6H) |
| 6.10 | (s, 2H) |

Figure 7:
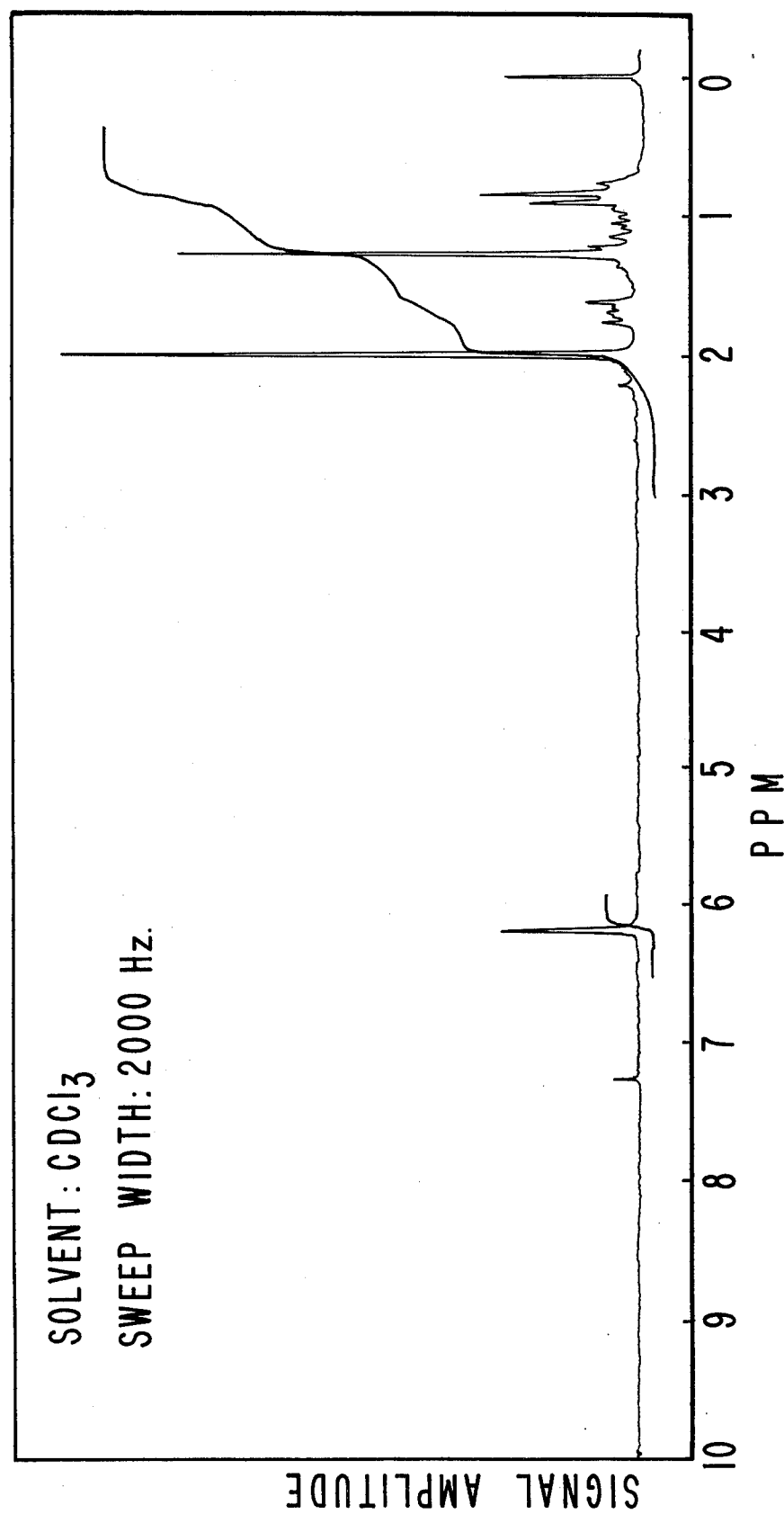
FIG. 7 represents the NMR spectrum for the compound 4-butyl-3,4,5-trimethyl-2,5-cyclohexadien-1-one, produced according to Example V.

FIG. 7 is the NMR spectrum

Mass Spectral Analysis (m/e) (order of intensity) 136, 121, 41, 29, 27, 91

EXAMPLE VI

The following mixture is prepared:

| Ingredients | Parts by Weight |
|---|---|
| Phenylacetic acid | 70.0 |
| Coumarin | 20.0 |
| Phenylethylphenyl acetate | 100.0 |
| Phenyl ethyl alcohol | 5.0 |
| Benzyl benzoate | 100.0 |
| Dimethylphenylethyl carbinol | 10.0 |
| Methyl anthranilate | 5.0 |
| Beta ionone | 10.0 |
| 2,4,4,6-tetramethyl-2,5-cyclohexadien-1-one | 30.0 |

The 2,4,4,6-tetramethyl-2,5-cyclohexadien-1-one imparts a warm, sweet, slightly minty, woody note to this honey formulation, and it enhances the herbaceous character thereof.

EXAMPLE VII

The following mixture is prepared:

| Ingredients | Parts by Weight |
|---|---|
| Para-cresol | 3.0 |
| Methyl N-acetylanthranilate | 20.0 |
| Farnesol | 3.0 |
| Nerolidol | 20.0 |
| Cis-3-hexenyl benzoate | 30.0 |
| Indol | 15.0 |
| Eugenol | 35.0 |
| Benzyl alcohol | 50.0 |
| Methyl linoleate | 100.0 |
| Jasmine lactone | 30.0 |
| Dihydro methyl Jasmonate | 20.0 |
| Benzyl acetate | 500.0 |
| Cis-Jasmone | 40.0 |
| Linalool | 200.0 |
| 4-butyl-3,4,5-trimethyl-2,5-cyclohexadien-1-one (prepared according to the process of Example V) | 50.0 |

The 4-butyl-3,4,5-trimethyl-2,5-cyclohexadien-1-one imparts a green, herbaceous, floralcy of Jasmine to this Jasmine formulation.

EXAMPLE VIII

PREPARATION OF A COSMETIC POWDER COMPOSITION

A cosmetic powder is prepared by mixing in a ball mill 100 g of talcum powder with 0.25 g of 2,4,4,6-tetramethylcyclohexa-2,5-diene-1-one prepared according to Example II. It has a warm, sweet, slightly minty, woody aroma.

EXAMPLE IX

PERFUMED LIQUID DETERGENT

Concentrated liquid detergents (Lysine salt of n-dodecylbenzene sulfonic acid as more specifically described in U.S. Pat. No. 3,948,818 issued on Apr. 6, 1976) with a warm, sweet, slightly minty, woody aroma are prepared containing 0.10%, 0.15% and 0.20% of 2,4,4,6-tetramethylcyclohexa-2,5-diene-1-one prepared according to Example II. They are prepared by adding and homogeneously mixing the appropriate quantity of 2,4,4,6-tetramethylcyclohexa-2,5-diene-1-one in the liquid detergent. The detergents all possess a warm, sweet, slightly minty, woody aroma, the intensity increasing with greater concentrations of 2,4,4,6-tetramethylcyclohexa-2,5-diene-1-one.

EXAMPLE X

PREPARATION OF A COLOGNE AND HANDKERCHIEF PERFUME 2,4,4,6-Tetramethylcyclohexa-2,5-diene-1-one -prepared according to the process of Example II is incorporated in a cologne at a concentration of 2.5% in 85% aqueous ethanol; and into a handkerchief perfume at a concentration of 20% (in 95% aqueous ethanol). A distinct and definite warm, sweet, slightly minty, woody aroma is imparted to the cologne and to the handkerchief perfume.

EXAMPLE XI

PREPARATION OF SOAP COMPOSITION

One hundred grams of soap chips are mixed with one gram of 2,4,4,6-tetramethylcyclohexa-2,5-diene-1-one of Example II until a homogeneous composition is obtained. The perfumed soap composition manifests a warm, sweet, slightly minty, woody aroma.

EXAMPLE XII

PREPARATION OF A DETERGENT COMPOSITION

A total of 100 g of a detergent powder (Lysine salt of n-dodecylbenzene sulfonic acid as more specifically described in U.S. Pat. No. 3,948,818 issued on Apr. 6, 1976) is mixed with 0.15 g of the 2,4,4,6-tetramethylcyclohexa-2,5-diene-1-one of Example II until a substantially homogeneous composition is obtained. This composition has a warm, sweet, slightly minty, woody aroma.

EXAMPLE XIII

PREPARATION OF A COSMETIC POWDER COMPOSITION

A cosmetic powder is prepared by mixing in a ball mill 100 g of talcum powder with 0.25 g of 4-butyl-3,4,5-trimethyl-2,5-cyclohexadien-1-one prepared according to Example V. It has a green, herbaceous, floral aroma.

EXAMPLE XIV

PERFUMED LIQUID DETERGENT

Concentrated liquid detergents (Lysine salt of n-dodecylbenzene sulfonic acid as more specifically described in U.S. Pat. No. 3,948,818 issued on Apr. 6, 1976) with a green, herbaceous, floral aroma are prepared containing 0.10%, 0.15% and 0.20% of 4-butyl-3,4,5-trimethyl-2,5-cyclohexadien-1-one prepared according to Example V. They are prepared by adding and homogeneously mixing the appropriate quantity of 4-butyl-3,4,5-trimethyl-2,5-cyclohexadien-1-one in the liquid detergent. The detergents all possess a green, herbaceous, floral aroma, the intensity increasing with greater concentrations of 4-butyl-3,4,5-trimethyl-2,5-cyclohexadien-1-one.

EXAMPLE XV

PREPARATION OF A COLOGNE AND HANDKERCHIEF PERFUME

4-Butyl-3,4,5-trimethyl-2,5-cyclohexadien-1-one prepared according to the process of Example V is incorporated in a cologne at a concentration of 2.5% in 85% aqueous ethanol; and into a handkerchief perfume at a concentration of 20% (in 95% aqueous ethanol. A distinct and definite green, herbaceous, floral aroma is imparted to the cologne and to the handkerchief perfume.

EXAMPLE XVI

PREPARATION OF SOAP COMPOSITON

One hundred grams of soap chips are mixed with one gram of 4-butyl-3,4,5-trimethyl-2,5-cyclohexadien-1-one of Example V until a substantially homogeneous composition is obtained. The perfumed soap composition manifests an excellent green, herbaceous, floral aroma.

EXAMPLE XVII

PREPARATION OF A DETERGENT COMPOSITION

A total of 100 g of a detergent powder (Lysine salt of n-dodecylbenzene sulfonic acid as more specifically described in U.S. Pat. No. 3,948,818 issued on Apr. 6, 1976) is mixed with 0.15% of the 4-butyl-3,4,5-trimethyl-1,2,5-cyclohexadien-1-one of Example V until a substantially homogenous composition is obtained. This composition has an excellent green, herbaceous, floral aroma.

EXAMPLE XVIII

PREPARATION OF A COLOGNE AND HANDKERCHIEF PERFUME

The composition of Example VI is incorporated in a cologne at a concentration of 2.5% in 85% aqueous ethanol; and into a handkerchief perfume at a concentration of 20% (in 95% aqueous ethanol). The use of 2,4,4,6-tetramethylcyclohexa-2,5-diene-1-one in the composition of Example VI affords a distinct and definite strong warm, sweet, slightly minty, woody aroma with a definite honey-like fragrance having a herbaceous character.

EXAMPLE XIX

PREPARATION OF A COLOGNE AND A HANDKERCHIEF PERFUME

The composition of Example VII is incorporated in a cologne at a concentration of 2.5% in 85% aqueous ethanol; and into a handkerchief perfume at a concentration of 20% (in 951 % aqueous ethanol). The use of 4-butyl-3,4,5-trimethyl-2,5-cyclohexadien-1-one in the composition of Example VII affords a strong Jasmine aroma with green, herbaceous and floral notes to the handkerchief perfume and cologne.

EXAMPLE XX

A white bread dough mix is prepared by mixing 1350 g of wheat flour and 800 ml water. To the mix is added:

| Ingredient | Amount (grams) |
|---|---|
| Yeast | 27.0 |
| Sodium chloride | 27.0 |
| Sucrose | 67.5 |
| Shortening | 54 |
| Non-fat dry milk powder | 40.5 |
| Yeast food (Arkady; manufactured by Fleischmann, Div. of Standard Brands) | 0.50 |
| Softening agents (succinylated monoglycerides; manufactured by Kraft Div. of National Dairy Products Corporation) | 3.4 |

Twelve grams of the product obtained in Example V, 4-butyl-3,4,5-trimethyl-2,5-cyclohexadien-1-one, are added to the dough. The dough is then mixed for 8 minutes and allowed to rise for 45 minuts at 40° C. The dough is then baked for 45 minutes at 210° C.

The breadstuff product obtained has a flavor note reminiscent of the crust of home-made Italian bread and has acceptable and persistent flavor properties for a period of one week and has good flavor characteristics when spread with margarine.

By way of comparison, breadstuffs similarly prepared but omitting the compound of Example V have a flat taste, show typical flavor deterioration on storage during a period of one week, and require an expensive butter spread to provide an acceptable flavor.

EXAMPLE XXI

A tobacco blend is made up by mixing the following materials:

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes, and the following formulation is compounded and incorporated into each of these cigarettes.

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with 2,4,4,6-tetramethylcyclohexa-2,5-diene-1-one produced according to Example II, at 100 ppm per cigarette. Another one-third of these model cigarettes are treated in the filter with the 2,4,4,6-tetramethylcyclohexa-2,5-diene-1-one produced according to Example II, at the rate of $2 \times 10^{-5}$ gm and $3 \times 10^{-5}$ gm. When evaluated by paired comparison, the cigarettes treated both in the tobacco and in the filter with the 2,4,4,6-tetramethylcyclohexa-2,5-diene-1-one are found, in smoke flavor, to be more tobacco-like with enhanced Virginia tobacco-like notes.

EXAMPLE XXII

A tobacco blend is made up by mixing the following materials:

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes, and the following formulation is compounded and incorporated into each of these cigarettes.

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with 4-buty-3,4,5-trimethyl-2,5-cyclohexadien-1-one produced according to Example V, at 100 ppm per cigarette. Another one-third of these model cigarettes is treated in the filter with the 4-butyl-3,4,5-trimethyl-2,5-cyclohexadien-1-one produced according to Example V at the rate of $2 \times 10^{-5}$ and $3 \times 10^{-5}$ gm. When evaluated by paired comparison, the cigarettes treated both in the tobacco and in the filter with the 4-butyl-3,4,5-trimethyl-2,5-cyclohexadien-1-one are found, in smoke flavor, to be similar to smoking a cigarette having dry black tobacco. In addition there are present in the aroma and taste on smoking pungent, spicey, celery black pepper-like and sweet nuances.

EXAMPLE XXIII

VANILLA FLAVOR FORMULATION

A basic vanilla flavor is prepared by admixing the following ingredients:

| Ingredient | Parts by Weight |
|---|---|
| Maltol | 2 |
| Vanillin | 20 |
| Ethyl Vanillin | 3 |
| Anisaldehyde (1% in Propylene Glycol) | 1 |
| Heliotropin (10% in Propylene Glycol) | 2 |
| Ethanol (95%) | 12 |
| Propylene Glycol | 60 |
| | 100 TOTAL |

The above flavor is divided into two parts. To the first portion 0.1% by weight of 4-butyl-3,4,5-trimethyl-2,5-cyclohexadien-1-one is added. To the second portion no additional ingredients are added. The two flavor formulations are compared at the rate of 0.05% in water and submitted to a bench panel for evaluations. All of the panel members prefer the vanilla flavor with the additional 4-butyl-3,4,5-trimethyl-2,5-cyclohexadien-1-one as having taste characteristics reminiscent to the vanilla bean, more woody notes and a longer lasting aftertaste.

EXAMPLE XXIV

TOMATO JUICE FORMULATION

The following tomato juice formulation is prepared by admixing the following ingredients:

| Ingredient | Parts by Weight |
|---|---|
| Maltol | 2 |
| Vanillin | 20 |
| Ethyl Vanillin | 3 |
| Anisaldehyde (1% in Propylene Glycol) | 1 |
| Heliotropin (10% in Propylene Glycol) | 2 |
| Ethanol (95%) | 12 |
| Propylene Glycol | 60 |
| TOTAL | 100 |

To a canned tomato juice (manufactured by Campbell Soup Company of Camden, N.J.; ingredients: pure tomato juice, slightly salted) at the rate of 2 ppm is added, 4-butyl-3,4,5-trimethyl-2,5-cyclohexadien-1-one, and is evaluated by a bench panel. The panel concludes that the spicey notes are increased, with more black pepper notes added both in aroma and taste, the aftertaste being fuller and pleasantly longer lasting.

What is claimed is:

1. A process for augmenting or enhancing the organoleptic properties of a foodstuff comprising the step of adding to said foodstuff from 0.5 parts per million up to about 100 parts per million based on the total composition of 4-butyl-3,4,5-trimethyl-2,5-cyclohexadiene-1-one.

2. A flavor augmenting or enhancing composition comprising (i) about 0.1% up to about 15% by weight based on the total weight of the composition of 4-butyl-3,4,5,-trimethyl-2,5-cyclohexadiene-1-one, and (ii) the remainder of said composition being a flavor adjuvant compound selected from the group consisting of p-hydroxybenzyl acetone; geraniol; cassia oil; acetaldehyde; maltol; ethyl methyl phenyl glycidate; benzyl acetate; dimethyl sulfide; eugenol, vanillin; caryophyllene; methyl cinnamate; guiacol; ethyl pelargonate; cinnamaldehyde; methyl anthranilate; 5-methylfurfural; isoamyl acetate; isobutyl acetate; cuminaldehyde; alpha ionone; cinnamyl formate; ethyl butyrate; methyl cinnamate; acetic acid; gammaundecalactone; naphthyl ethyl ether; diacetyl; furfural; ethyl acetate; anethole; 2,3-dimethyl pyrazine; 2-ethyl-3-methyl pyrazine; 3-phenyl-4-pentenal; 2-phenyl-2-hexenal 2-phenyl-2-pentenal; 3-phenyl-4-pentenal diethyl acetal; damascone (1-crotonyl-2,2,6-trimethylcyclohexen-1-one); damascenone (1-crotonyl-2,2,6-trimethylcyclohexa-1,5-diene); beta-cyclohomocitral (2,2,6-trimethylcyclohex-1-ene carboxaldehyde); isoamyl butyrate; cis-3-hexanol-1; 2-methyl-2-pentenoic acid; elemcine (4-allyl-1,2,6-trimethoxy benzene); isoelemecine (4-propenyl-1,2,6-trimethoxy-benzene); 2-(4-hydroxy-4-methylpentyl)-norbornadiene; reaction product of L-proline and 4-hydroxy-2,5-dimethyl-2(H)-furan-3-one; reaction product of ethyl maltol with L-proline; reaction product of cyclotene with L-proline; and reaction product of ethyl cyclotene with L-proline.

* * * * *